US012594040B2

(12) United States Patent
Cappon et al.

(10) Patent No.: US 12,594,040 B2
(45) Date of Patent: Apr. 7, 2026

(54) BAYESIAN FRAMEWORK FOR PERSONALIZED MODEL IDENTIFICATION AND PREDICTION OF FUTURE BLOOD GLUCOSE IN TYPE 1 DIABETES USING EASILY ACCESSIBLE PATIENT DATA

(71) Applicant: DexCom, Inc., San Diego, CA (US)

(72) Inventors: Giacomo Cappon, Padua (IT); Andrea Facchinetti, Trissino (IT); Giovanni Sparacino, Padua (IT); Simone Del Favero, Valle di Cadore (IT)

(73) Assignee: Dexcom, Inc., San Diego, CA (US)

( * ) Notice: Subject to any disclaimer, the term of this patent is extended or adjusted under 35 U.S.C. 154(b) by 519 days.

(21) Appl. No.: 17/454,693

(22) Filed: Nov. 12, 2021

(65) Prior Publication Data

US 2022/0233152 A1     Jul. 28, 2022

Related U.S. Application Data

(60) Provisional application No. 63/141,345, filed on Jan. 25, 2021.

(51) Int. Cl.
*A61N 1/00*          (2006.01)
*A61B 5/00*          (2006.01)
          (Continued)

(52) U.S. Cl.
CPC ........ *A61B 5/7275* (2013.01); *A61B 5/14532* (2013.01); *A61B 5/725* (2013.01); *G16H 50/30* (2018.01); *G16H 50/50* (2018.01)

(58) Field of Classification Search
None
See application file for complete search history.

(56) References Cited

U.S. PATENT DOCUMENTS 3,438,986 A * 4/1969 Zane .................. C08G 18/5075
                                                     544/196
6,280,381 B1 * 8/2001 Malin .................... G01N 21/49
                                                     128/920
(Continued)

FOREIGN PATENT DOCUMENTS

CN          104755019 A      7/2015
CN          106714874 B      10/2019
          (Continued)

OTHER PUBLICATIONS

Schiavon, M., Dalla Man, C., & Cobelli, C. (2018). Modeling subcutaneous absorption of fast-acting insulin in type 1 diabetes. IEEE Transactions on Biomedical Engineering, 65(9), 2079-2086 (Year: 2018).*

(Continued)

*Primary Examiner* — John R Downey
*Assistant Examiner* — Anant A Gupta
(74) *Attorney, Agent, or Firm* — PATTERSON + SHERIDAN, LLP

(57)          ABSTRACT
A method of predicting future blood glucose concentrations of an individual patient includes: selecting an individualized nonlinear physiological model of glucose-insulin dynamics, the selected model having a plurality of model parameters whose values are to be determined; estimating values for each of the model parameters in the plurality of model parameters, a first subset of the model parameters having values estimated from a priori population data and a second subset of the model parameters having values personalized for the individual patient by applying a parameter estimation technique to a priori information and data for the individual patient to obtain a posteriori information; and; applying a nonlinear prediction technique to the selected model using the estimated values for each of the model parameters to (Continued)

obtain a predicted blood glucose concentration of the individual patient at a future time.

20 Claims, 4 Drawing Sheets

(51) Int. Cl.
| | |
|---|---|
| *A61B 5/145* | (2006.01) |
| *G16H 50/30* | (2018.01) |
| *G16H 50/50* | (2018.01) |

(56) References Cited

U.S. PATENT DOCUMENTS

| | | | | |
|---|---|---|---|---|
| 7,727,147 | B1 * | 6/2010 | Osorio | A61M 5/14244 |
| | | | | 600/347 |
| 11,298,071 | B1 | 4/2022 | Saghafi et al. | |
| 2010/0262117 | A1 | 10/2010 | Magni et al. | |
| 2011/0098548 | A1 | 4/2011 | Budiman et al. | |
| 2011/0184267 | A1 * | 7/2011 | Duke | A61B 5/725 |
| | | | | 600/365 |
| 2013/0109944 | A1 | 5/2013 | Sparacino et al. | |
| 2014/0088393 | A1 * | 3/2014 | Bernstein | G16H 80/00 |
| | | | | 600/365 |
| 2014/0118138 | A1 | 5/2014 | Cobelli et al. | |
| 2014/0118166 | A1 | 5/2014 | Hampapuram et al. | |
| 2014/0309615 | A1 * | 10/2014 | Mazlish | A61B 5/4839 |
| | | | | 604/504 |
| 2016/0198988 | A1 | 7/2016 | Bhavaraju et al. | |
| 2016/0342754 | A1 | 11/2016 | Vettoretti et al. | |
| 2016/0354543 | A1 * | 12/2016 | Cinar | G16H 40/63 |
| 2017/0074757 | A1 | 3/2017 | Garcia et al. | |
| 2017/0224291 | A1 | 8/2017 | Hampapuram et al. | |
| 2017/0252513 | A1 * | 9/2017 | Buck, Jr. | A61B 5/14532 |
| 2018/0116573 | A1 | 5/2018 | Steiger et al. | |
| 2018/0174675 | A1 | 6/2018 | Roy et al. | |
| 2018/0184952 | A1 * | 7/2018 | Roy | A61B 5/725 |
| 2018/0192927 | A1 | 7/2018 | Taub et al. | |
| 2018/0272063 | A1 | 9/2018 | Neemuchwala et al. | |
| 2019/0114531 | A1 | 4/2019 | Torkamani et al. | |
| 2019/0328966 | A1 | 10/2019 | Chase et al. | |
| 2019/0336684 | A1 | 11/2019 | O'Connor et al. | |
| 2020/0237271 | A1 | 7/2020 | Vanslyke et al. | |
| 2020/0375549 | A1 | 12/2020 | Wexler et al. | |
| 2021/0038163 | A1 | 2/2021 | Agrawal et al. | |
| 2021/0050089 | A1 | 2/2021 | Mohammed et al. | |
| 2021/0100486 | A1 | 4/2021 | Romero Ugalde | |
| 2021/0275743 | A1 | 9/2021 | Romero Ugalde et al. | |
| 2021/0285819 | A1 | 9/2021 | Poli et al. | |
| 2021/0369151 | A1 | 12/2021 | Derdzinski et al. | |
| 2021/0375447 | A1 | 12/2021 | Derdzinski et al. | |
| 2021/0390399 | A1 | 12/2021 | Georgiou et al. | |
| 2022/0061676 | A1 | 3/2022 | Wilson et al. | |

FOREIGN PATENT DOCUMENTS

| | | | | |
|---|---|---|---|---|
| CN | 109480835 | B | 4/2021 | |
| EP | 3438986 | A1 * | 2/2019 | A61B 5/14532 |
| EP | 4280950 | A1 | 11/2023 | |
| JP | 2010531678 | A | 9/2010 | |
| JP | 2016136989 | A | 8/2016 | |
| JP | 2019513258 | A | 5/2019 | |
| WO | WO-2006075133 | A1 * | 7/2006 | A61B 5/0476 |
| WO | 2019180341 | A1 | 9/2019 | |
| WO | 2019213493 | A1 | 11/2019 | |
| WO | 2020002848 | A1 | 1/2020 | |
| WO | 2020089656 | A1 | 5/2020 | |
| WO | 2020187987 | A1 | 9/2020 | |

OTHER PUBLICATIONS

Visentin, R., Campos-Náñez, E., Schiavon, M., Lv, D., Vettoretti, M., Breton, M., Kovatchev, B. P., Dalla Man, C., & Cobelli, C. (2018). The UVA/padova type 1 diabetes simulator goes from single meal to Single Day. Journal of Diabetes Science and Technology, 12(2), 273-281 (Year: 2018).*

Åström, K. J. (1980). Maximum likelihood and prediction error methods. Automatica, 16(5), 551-574 (Year: 1980).*

Man, C. D., Camilleri, M., & Cobelli, C. (2006). A system model of oral glucose absorption: Validation on gold standard data. IEEE Transactions on Biomedical Engineering, 53(12), 2472-2478 (Year: 2006).*

International Preliminary Report on Patentability for Application No. PCT/US2021/059235, mailed Aug. 3, 2023, 7 pages.

Cappon G., et al., "A Bayesian Framework to Identify Type 1 Diabetes Physiological Models Using Easily Accessible Patient Data," 2019 41st Annual International Conference of the IEEE Engineering in Medicine and Biology Society (EMBC), Jul. 23, 2019, Retrieved on Jan. 10, 2022 from URL: https://ieeexplore.ieee.org/abstract/document/8856846, 4 pages.

Contreras I., et al., "Personalized Blood Glucose Prediction: A Hybrid Approach Using Grammatical Evolution and Physiological Models," PloS one, Nov. 7, 2017, Retrieved on Jan. 10, 2022 from URL: https://journals.plos.org/plosone/article/comments?id=10.1371/journal.pone.0187754, 16 pages.

Eren-Oruklu M., et al., "Adaptive System Identification for Estimating Future Glucose Concentrations and Hypoglycemia Alarms," Automatica, vol. 48(8):1892-1897, Jun. 22, 2012, Retrieved on Jan. 10, 2022 from URL: www.ncbi.nlm.nih.gov/pmc/articles/PMC3409594/, 15 pages.

International Search Report and Written Opinion for Application No. PCT/US2021/059235, mailed Feb. 7, 2022, 17 pages.

International Search Report and Written Opinion dated Feb. 25, 2021 for Application No. PCT/US2020/063437, filed Dec. 4, 2020, 10 pages.

International Preliminary Report on Patentability for Application No. PCT/US2020/063437, mailed Dec. 8, 2022, 8 pages.

Chen M., et al., "5G-Smart Diabetes: Toward Personalized Diabetes Diagnosis with Healthcare Big Data Clouds," IEEE Communications Magazine, Apr. 2018, vol. 56, No. 04, pp. 16-23.

Schwartz F.L., et al., "The Promise and Perils of Wearable Physiological Sensors for Diabetes Management," Journal of Diabetes Science and Technology, Mar. 15, 2018, vol. 12, No. 03, pp. 587-591.

* cited by examiner

BAYESIAN FRAMEWORK FOR PERSONALIZED MODEL IDENTIFICATION AND PREDICTION OF FUTURE BLOOD GLUCOSE IN TYPE 1 DIABETES USING EASILY ACCESSIBLE PATIENT DATA

INCORPORATION BY REFERENCE TO RELATED APPLICATION

Any and all priority claims identified in the Application Data Sheet, or any correction thereto, are hereby incorporated by reference under 37 CFR 1.57. This application claims the benefit of U.S. Provisional Patent Application No. 63/141,345, filed Jan. 25, 2021. This application relates to U.S. application Ser. Nos. 17/112,870, 17/112,828, and 17/112,814, all filed Dec. 4, 2020. The aforementioned applications are incorporated by reference herein in their entirety, and are hereby expressly made a part of this specification.

BACKGROUND

Type 1 diabetes (T1D) is a chronical autoimmune disease caused by the progressive destruction of beta cells in the pancreas, which leads to the inability of producing endogenous insulin by the organism. As a result, blood glucose (BG) concentration tends to exceed the hyperglycemic threshold (BG>180 mg/dl), a situation that, if frequent and prolonged, could lead to several serious cardiovascular long-term complications, as well as nephropathy and neuropathy. To reduce BG levels, administration of exogenous insulin several times a day is necessary. Unfortunately, excessive exogenous insulin dosing could lead patients to hypoglycemia, i.e., BG<70 mg/dl, which is dangerous even in the short-term since it could cause fainting, light-headiness, coma and even death.

Effective T1D treatment relies on BG frequent monitoring, made through either the classic fingerstick device or more modern minimally invasive continuous glucose monitoring (CGM) sensors, and is far from being trivial. Indeed, T1D management represents, from a patient perspective, a life-long learning process to understand how several everyday factors (e.g., illness, diet, and physical activity) affect BG levels and how interventions (e.g., rescue carbohydrate intake and, of course, insulin administration) can be used to keep BG in the safe range.

In this context, many efforts have been made by the research community to provide new tools able to help patients with T1D. Among them, CGM-based algorithms able to predict future BG concentration in real-time have the potential to significantly improve T1D therapy efficacy by enabling proactive therapeutic decisions based on the expected future glucose levels, rather than the current one.

SUMMARY

In a first aspect, a method is provided of predicting future blood glucose concentrations of an individual patient, comprising: selecting an individualized nonlinear physiological model of glucose-insulin dynamics, the selected model having a plurality of model parameters whose values are to be determined; estimating values for each of the model parameters in the plurality of model parameters, a first subset of the model parameters having values estimated from a priori population data and a second subset of the model parameters having values personalized for the individual patient by applying a parameter estimation technique to a priori information and data for the individual patient to obtain a posteriori information; and; applying a nonlinear prediction technique to the selected model using the estimated values for each of the model parameters to obtain a predicted blood glucose concentration of the individual patient at a future time.

In an embodiment of the first aspect, the parameter estimation technique is a Markov Chain Monte Carlo (MCMC) Bayesian estimator.

In an embodiment of the first aspect, the parameter estimation technique is selected from the group consisting of a maximum a posteriori technique, a maximum likelihood technique and a prediction error minimization technique.

In an embodiment of the first aspect, the nonlinear prediction technique is a particle filter.

In an embodiment of the first aspect, the nonlinear prediction technique is a particle filter.

In an embodiment of the first aspect, the nonlinear prediction technique is selected from the group consisting of an extended Kalman filter technique and an unscented Kalman filter technique.

In an embodiment of the first aspect, the nonlinear prediction technique is selected from the group consisting of an extended Kalman filter technique and an unscented Kalman filter technique.

In an embodiment of the first aspect, the selected individualized nonlinear physiological model includes a subcutaneous insulin absorption sub-model, an oral glucose absorption sub-model and a glucose-insulin kinetics model.

In an embodiment of the first aspect, the selected individualized nonlinear physiological model uses past blood glucose concentration levels, carbohydrate intake information and exogenous insulin data of the individual patient as inputs.

In an embodiment of the first aspect, the subcutaneous insulin absorption sub-model includes a first model parameter specifying a value of insulin distribution and a second model parameter specifying a delay in an appearance of insulin in a first compartment, the first and second model parameters being in the first subset of model parameters having values estimated from the a priori population data.

In an embodiment of the first aspect, the subcutaneous insulin absorption sub-model includes a third model parameter specifying a diffusion rate constant from a first to a second compartment and a fourth model parameter specifying a rate constant of subcutaneous insulin absorption from the second compartment to plasma, the third and fourth model parameters being in the second subset of model parameters having values personalized for the individual patient.

In an embodiment of the first aspect, the selected individualized nonlinear physiological model is a maximal physiological model in which selected ones of the model parameters are neglected.

In an embodiment of the first aspect, the predicted blood glucose concentration is updated in real-time using real-time continuous glucose monitor (CGM) data, carbohydrate intake information and exogenous insulin data In an embodiment of the first aspect, the method further includes augmenting the selected individualized nonlinear physiological model with a residual error model to describe residual modeling errors.

In an embodiment of the first aspect, the residual modeling errors are modeled as an Auto regressive Integrated Moving Average (ARIMA) of order (5,5,1).

In an embodiment of the first aspect, the residual error model has model parameters estimated using a predicted error method (PEM).

In an embodiment of the first aspect, the predicted blood glucose concentration is predicted at a plurality of different times.

DETAILED DESCRIPTION

I. Introduction

Despite several different methodologies having been proposed for blood glucose (BG) real-time prediction, the problem remains open due to several unknown disturbances altering BG levels and to the high inter-/intra-patient variability in glucose physiology. The existing prediction techniques rely on a mathematical model which describes the relationship between a certain set of input features and BG. The choice of a suitable model of glucose-insulin regulation is an important step and the options spans from "black-box" models, completely data-driven, to models based on mechanistic/semi-mechanistic nonlinear description of metabolic physiology. Compared to black-box models, physiological models have the clear advantage of guaranteeing to correctly capture the underneath glucose-insulin metabolism mechanisms. Among the nonlinear physiological models available in the T1D literature, the so-called minimal models prove too rigid and simplistic to grant effective glucose prediction. On the other hand, large-scale models have several equations and multiple parameters which make them hardly identifiable and more suited to computer simulations than to model-based prediction.

Figure 1:
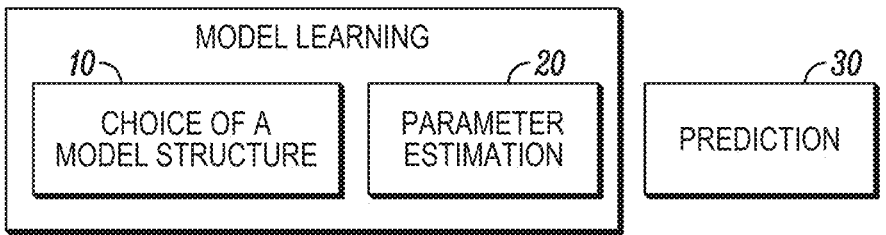
FIG. 1 is flowchart illustrating at a high level the steps involved in the individualized model-based prediction scheme described herein.

FIG. 1 is flowchart illustrating at a high level the steps involved in the individualized model-based prediction scheme described herein. As shown, the first step 10 in the scheme selects a suitable model structure from among the various available options described above. The selected model is an individualized nonlinear physiological model of glucose-insulin regulation. As described below, the selected model has model parameters that can be individualized from easily accessible patient logs, such as carbohydrate intake and insulin infusion data, to mimic an individual specific physiology.

In the second step 20 of the prediction scheme shown in FIG. 1 selected ones of the model parameters that are to be personalized for an individual patient are estimated using a parameter estimation technique. In one embodiment the parameter estimation technique that is used employs a Bayesian approach, implemented by Markov Chain Monte Carlo (MCMC) to estimate the large number of parameters in the presence of complex nonlinear dynamics. Next, in the third step 30 the obtained personalized model is used within a nonlinear prediction scheme based, for example, on a particle filter methodology.

As will be further described in more detail below, the prediction scheme described herein is tested using an in silico clinical trial comprising data of 100 virtual T1D patients generated by a simulation model described in R. Visentin, E. Campos-Nuñez, M. Schiavon, D. L v, M. Vettoretti, M. Breton, B. P. Kovatchev, C. Dalla Man, and C. Cobelli, "The uva/padova type 1 diabetes simulator goes from single meal to single day," J. Diabetes Sci. Technol., vol. 12, no. 2, pp. 273-281, 2018, which is hereby incorporated by reference in its entirety. For comparison, two baseline black-box models are considered. The metrics chosen for the assessment are the root mean square error, the coefficient of determination, and the time gain. Results show that the proposed approach is superior than both baseline methodologies in predicting future glucose concentration especially in terms of time gain.

II. A Physiological Model of Glucose-Insulin Regulation

This section describes one example of a nonlinear physiological model of glucose-insulin dynamics for personalized glucose prediction. This example starts from the maximal physiological model implemented in the most recent version of the UVa/Padova T1D Simulator (T1DS) described in the Visentin et al. reference cited above. and simplifies it as much as possible to reduce the number of parameters to be estimated for individualization while retaining its ability to achieve good glucose prediction.

The proposed model has two inputs, insulin infusion I(t), and carbohydrate intake CHO(t), and one output, the interstitial glucose concentration IG(t). The model is composed of three subsystems describing subcutaneous insulin absorption, oral glucose absorption, and glucose-insulin kinetics.

A. Subcutaneous Insulin Absorption Subsystem

Figure 2:
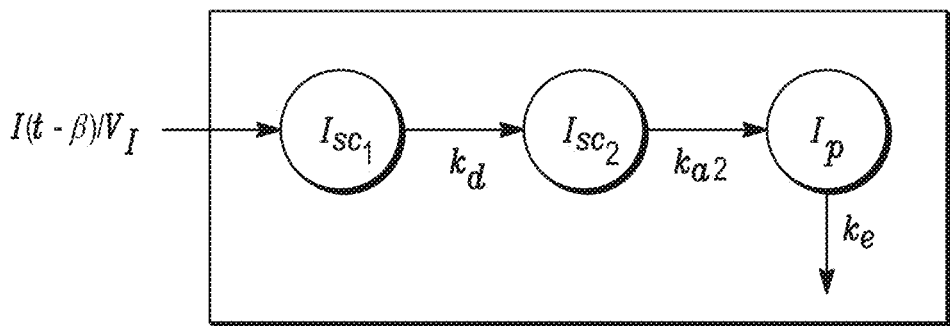
FIG. 2 illustrates one example of the subcutaneous insulin absorption subsystem scheme.

The subcutaneous insulin absorption model is a slightly simplified version of the one used in the T1DS model, described in M. Schiavon, C. Dalla Man, and C. Cobelli, "Modeling subcutaneous absorption of fast-acting insulin in type 1 diabetes," IEEE Trans. Biomed. Eng., vol. 65, no. 9, pp. 2079-2086, 2018 and illustrated in FIG. 2. The model is composed of three compartments. Exogenous insulin I is infused to the first compartment where it appears after a delay β. In the first compartment, representing insulin in a non-monomeric state, insulin is transformed in a monomeric state and then diffused to the plasma. The model equations are:

$$\begin{cases} \dot{I}_{sc1}(t) = -k_d \cdot I_{sc1}(t) + I(t-\beta)/V_I \\ \dot{I}_{sc2}(t) = k_d \cdot I_{sc1}(t) - k_{a2} \cdot I_{sc2}(t) \\ \dot{I}_p(t) = k_{a2} \cdot I_{sc2} - k_e \cdot I_p(t) \end{cases} \tag{1}$$

where $I_{sc1}$ (mU/kg) and $I_{sc2}$ (mU/kg) represent the insulin in a non-monomeric and monomeric state, respectively; $I_p$ (mU/l) is the plasma insulin concentration; $k_d$ (min$^{-1}$) is the rate constant of diffusion from the first to the second compartment; $k_{a2}$ (min$^{-1}$) is the rate constant of subcutaneous insulin absorption from the second compartment to the plasma; $k_e$ (min$^{-1}$) is the fractional clearance rate; $V_I$ (l/kg)

is the volume of insulin distribution; $\beta$ (min) is the delay in the appearance of insulin in the first compartment. The simplification with respect to the model used in the T1DS consists in neglecting the fact that a fraction of non-monomeric insulin can reach the plasma directly. This absorption route is depicted in gray in FIG. 1 and associated to the rate constant $k_{a1}$. The simplification is due to the fact that both the insulin fraction and the number of patients where this happens is small. A priori information on model parameters, reported in Table 1, have been obtained from the literature. Specifically, $V_I$ and $\beta$ have been set to population values, i.e. 0.126 l/kg and 8 min, respectively. Furthermore, $k_d$ has been constrained to $k_d \geq k_{a2}$ since the two combinations are interchangeable. Unknown model parameters result $\theta_{ins} = [k_{a2}, k_d]$.

B. Oral Glucose Absorption Subsystem

Figure 3:
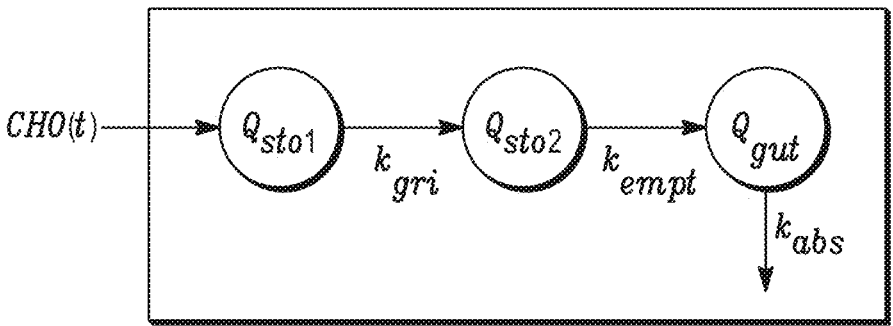
FIG. 3 illustrates one example of the oral glucose absorption subsystem scheme.

The oral glucose absorption subsystem model, taken from C. Dalla Man, M. Camilleri, and C. Cobelli, "A system model of oral glucose absorption: Validation on gold standard data," IEEE Trans. Biomed. Eng., vol. 53, no. 12, pp. 2472-2478, 2006, represents a simplified version of the model used in the T1DS and is illustrated in FIG. 3. It describes the gastro-intestinal tract as three-compartment system: the first two compartments account for food in the stomach (solid and grinded state), while the third compartment models the upper small intestine where CHO is absorbed. Model equations are:

$$\begin{cases} \dot{Q}_{sto1}(t) = -k_{gri} \cdot Q_{sto1}(t) + CHO(t) \\ \dot{Q}_{sto2}(t) = k_{gri} \cdot Q_{sto1}(t) - k_{empt} \cdot Q_{sto2}(t) \\ \dot{Q}_{gut}(t) = k_{empt} \cdot Q_{sto2}(t) - k_{abs} \cdot Q_{gut}(t) \end{cases} \quad (2)$$

where $Q_{sto1}$ (mg/kg) and $Q_{sto2}$ (mg/kg) are the glucose amount in the stomach in a solid and liquid state, respectively; $Q_{gut}$ (mg/kg) is the glucose concentration in the intestine; $k_{gri}$ (min$^{-1}$) is the rate constant of grinding; $k_{empt}$ (min$^{-1}$) is the rate constant of gastric emptying; $k_{abs}$ (min$^{-1}$) is the rate constant of intestinal absorption; CHO (mg/kg/min) is the ingested carbohydrate rate. Model (2) allows to estimate the rate of glucose appearance in plasma Ra (mg/kg/min) as:

$$Ra(t) = f \cdot k_{abs} \cdot Q_{gut}(t) \quad (3)$$

where f (dimensionless) is the fraction of the intestinal content absorbed in the plasma.

The simplification with respect to the model used in the T1DS consists in assuming a constant gastric emptying rate, thus neglecting its dependence on stomach content (depicted in gray in FIG. 3).

A priori information on model (2) has been obtained from the literature and has been detailed in Table 1. In particular, we set f equal to 0.9 and we constrained $k_{gri} = k_{empt}$. Furthermore, $k_{abs}$ has been constrained to $k_{abs} \leq k_{empt}$ since the two combinations are interchangeable. As such, the unknown model parameters are $\theta_{oral} = [k_{abs}, k_{empt}]$.

C. Glucose-Insulin Kinetics Subsystem

Figure 4:
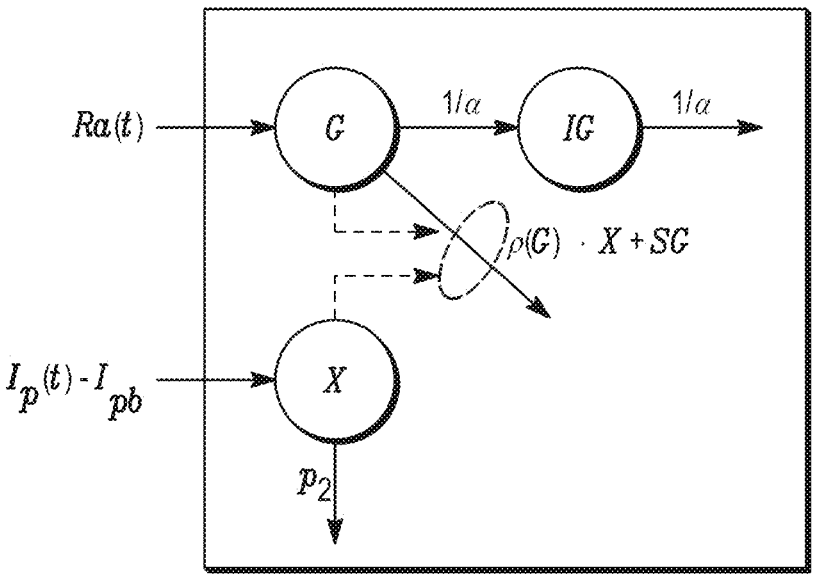
FIG. 4 illustrates one example of the glucose-insulin kinetics subsystem scheme.

With respect to the model used in the T1DS simulator, we used a more parsimonious description of the glucose-insulin kinetics subsystem. It is based on a well-known two-compartment model that describes the impact of the plasmatic insulin action and glucose rate of appearance in plasma glucose concentration introduced in R. N. Bergman, C. R. Bowden, and C. Cobelli, "Quantitative estimation of insulin sensitivity," Am. J. Physiol., vol. 236, no. 6, pp. e667-e677, 1979. The model is further equipped with a third compartment to describe the transport of glucose from plasma to the interstitium where it is measured by the sensor. The model is illustrated in FIG. 4. Model equations are:

$$\begin{cases} \dot{G}(t) = -[SG + \rho(G)X(t)] \cdot G(t) + SG \cdot G_b + Ra(t)/V_G \\ \dot{X}(t) = -p_2 \cdot [X(t) - SI \cdot (I_p(t) - I_{pb})] \\ \dot{IG}(t) = -\frac{1}{\alpha}(IG(t) - G(t)) \end{cases} \quad (4)$$

where G (mg/dl) is the plasma glucose concentration, X (min$^{-1}$) is the insulin action on glucose disposal and production; SG (min$^{-1}$) is the glucose effectiveness describing glucose ability, per se, to promote glucose disposal and inhibit glucose production; $G_b$ (mg/dl) is the basal glucose concentration in the plasma; $V_G$ (dl/kg) is the volume of glucose distribution; $p_2$ (min$^{-1}$) is the rate constant of insulin action dynamics; SI (ml/$\mu$U·min) is the insulin sensitivity; $I_{pb}$ (mU/l) is the basal insulin concentration in the plasma; IG (mg/di) is the interstitial glucose concentration; $\alpha$ (min) is the delay between the plasmatic and interstitial glucose concentration compartments.

The above model, with a constant unitary $\rho$, $\rho(G) \equiv 1 \ \forall G$, is known to struggle in capturing hypoglycemia, likely due to an inadequate description of insulin action, which was proved to increase when glucose decreases below a certain threshold. For this reason, following the rationale proposed in C. Dalla Man, F. Micheletto, D. L v, M. Breton, B. Kovatchev, and C. Cobelli, "The uva/padova type 1 diabetes simulator: New features," J. Diabetes Sci. Technol., vol. 8, no. 1, pp. 26-34, 2017, we introduce in the above model the term $\rho(G)$:

$$\rho(G) = \begin{cases} 1 & \text{if } G \geq G_b \\ 1 + 10 \cdot r_1 \{[\ln(G)]^{r_2} - [\ln(G_b)]^{r_2}\}^2 & \text{if } G_{th} < G < G_b \\ 1 + 10 \cdot r_1 \{[\ln(G_{th})]^{r_2} - [\ln(G_b)]^{r_2}\}^2 & \text{if } G \leq G_{th} \end{cases} \quad (5)$$

where $G_{th}$ is the hypoglycemic threshold (set to 60 mg/dl) and $r_1$ (dimensionless) and $r_2$ (dimensionless) are two model parameters with no direct physiological interpretation.

To account for patient-specific intraday insulin sensitivity variability and to model the so-called dawn phenomenon, the parameters SI and $G_b$ are considered time-varying over the day:

$$SI = \begin{cases} SI_B & \text{if } 4 \text{ AM} < t \leq 11 \text{ AM} \\ SI_L & \text{if } 4 \text{ AM} < t \leq 5 \text{ PM} \\ SI_D & \text{otherwise} \end{cases} \quad (6)$$

$$G_b = \begin{cases} G_{b_{dawn}} & \text{if } 2 \text{ AM} < t \leq 6 \text{ AM} \\ G_{b_{day}} & \text{otherwise} \end{cases} \quad (7)$$

A priori information on parameter distributions, reported in detail in Table 1, has been obtained from the literature. In detail, $r_1$, $r_2$, and $V_G$ have been fixed to population values, i.e. 1.44, 0.81, and 1.45 dl/kg respectively. Unknown model parameters of glucose-insulin subsystem are $\theta_{glu} = [SG, SI_B, SI_L, SI_D, G_{b_{dawn}}, G_{b_{day}}, p_2]$.

D. Overall Physiological Model

In summary, the overall physiological model is obtained combining the three submodels introduced so far:

$$\begin{cases} \dot{x}_{phy}(t) = f_{phy}(x_{phy}, u_{phy}, t, \theta_{phy}) \\ y(t) = IG(t) \end{cases} \tag{8}$$

where $x_{phy}$ (t) is the state vector defined as $$x_{phy}(t) :=$$

$$[x_{ins}, |x_{oral}, |x_{glu}]^T = [I_{sc1}, I_{sc2}, I_p, |Q_{sto1}, Q_{sto2}, Q_{gut}, |G, X, IG]^T;$$

$u_{phy}(t) := [I(t), CHO(t)]$ is the input vector;

$f_{phy}(\bullet)$ is the state update function obtained combining (1)-(5).

$f_{phy}(\bullet)$ depends on the set of unknown parameters $$\theta_{phy} := [\theta_{ins}, \theta_{oral}, \theta_{glu}]$$

whose estimation will be discussed in the next section.

TABLE 1

A Priori Information on Model Parameters

| Parameter | Distribution | Reference |
|---|---|---|
| SG | LOGN(−3.8, 0.5) | (30) |
| $SI_B$ | GAMMA(3.3, 4.5e−4) | (30) |
| $SI_L$ | GAMMA(3.3, 4.5e−4) | (30) |
| $SI_D$ | GAMMA(3.3, 4.5e−4) | (30) |
| $G_{b_{dawn}}$ | N(120, 5) | (30) |
| $G_{b_{day}}$ | N(120, 5) and $G_{b_{day}} \le G_{b_{dawn}}$ | (30) |
| sqrt($p_2$) | N(0.11, 0.004) | (30) |
| $k_{a2}$ | LOGN(−4.29, 0.43) and $k_d \ge k_{a2}$ | (24) |
| $k_d$ | LOGN(−3.51, 0.62) and $k_d \ge k_{a2}$ | (24) |
| $k_{abs}$ | LOGN(−5.46, 1.44) and $k_{abs} \le k_{empt}$ | (25) |
| $k_{empt}$ | LOGN(−1.96, 0.71) and $k_{abs} \le k_{empt}$ | (25) |

N(μ, σ) stands for a normal distribution of mean μ and standard deviation σ. LOGN(μ, σ) stands for a log-normal distribution of mean μ and standard deviation σ. GAMMA(a, b) stands for a gamma distribution with shape parameter a and scale parameter b.

III. Offline Bayesian Estimation of Personalized Model Parameters by Markov Chain Monte Carlo Model personalization has been performed by identifying for each patient the unknown model parameters $\theta_{phy}$ using the training data Y:={CGM($t_k$), $t_k$=k·$T_s$, k=1, . . . , D} and U:={$u_{phy}(t_k)$, $t_k$=k·$T_s$, k=1, . . . , D} where D is the number of data points available.

The identification has been performed by adopting a Bayesian approach and specifically, in this work $\theta_{phy}$ is estimated through its posterior mean defined as $$\hat{\theta}_{phy} = E[\theta_{phy}|Y,U] = \int \theta p_{\theta|Y,U}(\theta|Y,U)d\theta \tag{9}$$

Since the posterior mean is known to be the minimum variance unbiased estimator of $\theta_{phy}$.

The Bayes theorem allows to obtain the a posteriori density function $p_{\theta|Y,U}(\theta|Y,U)$ as:

$$p_{\theta|Y,U}(\theta \mid Y, U) = \frac{p_{Y|\theta,U}(Y \mid \theta, U)p_\theta(\theta)}{\int p_{Y|\theta,U}(Y \mid \theta, U)p_\theta(\theta)d\theta} \tag{10}$$

where $p_{Y|\theta,U}(Y|\theta,U)$ is the likelihood function, i.e., the probability of observing a certain Y given the parameter vector θ and the input U.

Since the integral in (9) is analytically intractable, it has to be approximated by resorting to MCMC. In particular, we generate N samples $\theta_i$, i=1, . . . , N from the posterior distribution $p_{\theta|Y,U}(\theta|Y,U)$ by creating a Markov Chain whose stationary distribution is exactly this posterior (target distribution). Then, these samples $\theta_i$ are used to perform Monte Carlo integration to obtain a point estimate of $\theta_{phy}$:

$$\hat{\theta}_{phy} = \frac{1}{N}\sum_i^N \theta_i. \tag{11}$$

To build such a chain, the Single Component Metropolis-Hastings (SCMH) algorithm has been used.

A. Implementation Details

We partitioned $\theta_{phy}$ into five sets $\theta_{phy} := [\theta_1, \theta_2, \theta_3, \theta_4, \theta_5]$, namely $\theta_1 := [SG, SI_B, G_{b_{dawn}}]$, $\theta_2 := [SI_L, G_{b_{day}}]$, $\theta_3 := [SI_D]$, $\theta_4 := [p_2, k_{a2}, k_d]$, $\theta_5 := [k_{empt}, k_{abs}]$. This partitioning scheme has been chosen since it improves MC mixing and allows to break the correlation between SI and $p_2$, known to be critical from the literature.

An iteration i of the algorithm consists of five steps p=1, . . . , 5 and each step updates the p-th partition of $\theta_{phy}$, $\theta_p$, by approval/rejection of a sample $\phi_p$ extracted from the proposal density function $q_p(\bullet|\bullet)$. Specifically, as prescribed by the SCMH procedure, approval occurs with probability α

$$\alpha = \min\left(1, \frac{\pi(\phi_p \mid \theta_{i,-p})q_p(\theta_{i-1,p} \mid \phi_p, \theta_{i,-p})}{\pi(\theta_{i-1,p} \mid \theta_{i,-p})q_p(\phi_p \mid \theta_{i-1,p}, \theta_{i,-p})}\right)$$

with $\pi(\theta_p|\theta_{i,-p})$ proportional to the posterior of $\theta_p$ given that the other components $\theta_{-p}$ assume the value $\theta_{-p} = \theta_{i,-p}$:

$$\pi(\theta_p|\theta_{i,-p}) = p_{Y|\theta,U}(Y|\theta_p, \theta_{i,-p}, U)p_\theta(\theta_p|\theta_{i,-p}, U)$$

$\theta_{i,-p}$ comprises all the other components of $\theta_{phy}$ except for $\theta_p$. Precisely, $\theta_{i,-p}$ contains the most updated version of each component as available at the current stage of the algorithm: $\theta_{i,-p} = [\theta_{i,1}, \ldots, \theta_{i,p-1}, \theta_{i-1,p+1}, \theta_{i-1,5}]$. Components up to p−1 have already been updated when processing the p-th components at iteration i, while other components, from p+1 to 5, have not been updated yet, so their value computed in the previous iteration i−1 is used.

For what it concerns the proposal distribution, we used a Gaussian centered in the value assumed by $\theta_p$ in the previous chain iteraction $$q_p(\bullet|\bullet) = N(\theta_{i-1,p}, \Sigma_p);$$

where $\Sigma_p$ is a tuning parameter that regulates the acceptance rate of the chain. We set $\Sigma_p$ to a diagonal matrix whose components are an estimate of the conditional standard deviation of each element of partition p, sd ($\theta_{phy_p}$|Y, U), multiplied by a scaling factor $2.4/\sqrt{d}$ as suggested in H. Haario, E. Saksman, and J Tamminen, "Adaptive proposal distribution for random walk metropolis algorithm," Computational Statistics, vol. 14, pp. 375-395, 1999. This estimates is computed by running two exploratory MCMCs for nIter=600 iterations and updated every 1500 iterations of the algorithm, thus implementing an adaptive SCMH.

Finally, the convergence of the MCMC has been verified through the well-known Raftery-Lewis criterion, which provides the number of iterations necessary to ensure the Markov Chain to represent the target posterior distribution.

The Adaptive Single Component Metropolis Hasting is summarized in Algorithm (1).

Algorithm 1: Adaptive Single Component Metropolis
Hastings

```
i ← 0;
initialize θ_phy0, nIter;
repeat
|       for p ← 1 to 5 do
|       |       set θ_phyi,-p =
|       |       [θ_phyi,1, . . . , θ_phyi,p-1, θ_phyi-1,p+1, θ_phyi-1,5];
|       |       sample φ_p ~ q_p(·|·);
|       |       set
|       |
|       |       α = min(1, π(φ_p|θ_i,-p)q_p(θ_i-1,p|φ_p, θ_i,-p) / π(θ_i-1,p|θ_i,-p)q_p(φ_p|θ_o-1,p, θ_i,-p))
|       |
|       |       sample U ~ Uniform(0, 1);
|       |       if U ≤ α then
|       |       |       set θ_phyi,p = φ_p;
|       |       else
|       |       |       set θ_phyi,p = θ_phyi-2,p
|       |       end
|       end
|       i ← i + 1
until n < nIter;
```

IV. Residual Error Model

Figure 5:
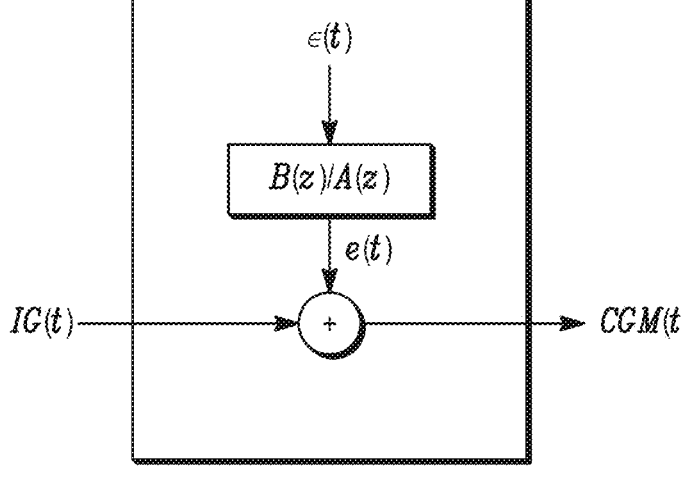
FIG. 5 illustrates one example of the residual error model scheme.

As a final step, the measured output CGM(t) is obtained by corrupting the output of the physiological model IG(t) with a stochastic error e(t) using the residual error model scheme of FIG. 5.

$$CGM(t)=IG(t)+e(t). \tag{12}$$

e(t) (mg/dl) describes the residual modelling errors and the measurement errors introduced by the CGM sensor. It is a colored random process that we model as an Auto Regressive Integrated Moving Average (ARIMA) of order (5,5,1):

$$e(t)=\Sigma_{i=1}^{6}a_i \cdot e(t-i)+\Sigma_{i=1}^{5}b_i \cdot \in(t-i)+\in(t) \tag{13}$$

where $\{a_i\}_{i=1,\ldots,6}$ and $\{b_i\}_{i=1,\ldots,5}$ are the coefficients of the model, and $\in(t)$ (mg/dl) is a white noise having zero-mean and constant standard deviation $SD_\in$. Since we are considering an ARIMA, one of the zeros of the denominator is in 1.

Model orders have been chosen to keep the model as simple as possible but still able describing well the residuals error e(t). Model parameters are estimated using the standard Prediction Error Method (PEM).

A. Augmented Model

The final model is then obtained augmenting (8) with the state space representation of the residual error model:

$$\begin{cases} x_{phy}(t_k) = f_d(x_{phy}, u_{phy}, t_{k-1}, \theta_{phy}) + v_{phy} & (14a) \\ (t_k) = Ae(t_{k-1}) + B\in(t_k) & (14b) \\ y(t_k) = IG(t_k) + Ce(t_k) + \in(t_k) & (14c) \end{cases}$$

where $f_d$ is obtained by discretizing $f_{phy}(x_{phy}, u_{phy}, t, \theta_{phy})$ using the Backward Euler method with $t_k=k \cdot T_S$ and further assumed to be corrupted by a model error $v_{phy}$, an i.i.d Gaussian process with covariance $\Sigma_{v_{phy}}$. The model is augmented with e, the state vector associated with a state-space representation of the ARIMA process describing the residual error (13) where matrices A, B, and C are defined as in G. E. P. Box, G. M. Jenkins, G. C. Reinsel, and G. M. Ljung, "Timeseries analysis: Forecasting and control," 5th edition. Hoboken, NJ: Wileyand Sons, 2015.

$$A = \begin{bmatrix} 0 & 1 & 0 & 0 & 0 & 0 \\ 0 & 0 & 1 & 0 & 0 & 0 \\ 0 & 0 & 0 & 1 & 0 & 0 \\ 0 & 0 & 0 & 0 & 1 & 0 \\ 0 & 0 & 0 & 0 & 0 & 1 \\ a_6 & a_5 & a_4 & a_3 & a_2 & a_1 \end{bmatrix}$$

$$B = \begin{bmatrix} 1 \\ b_1 \\ b_2 \\ b_3 \\ b_4 \\ b_4 \end{bmatrix}$$

$$C = [1 \; 0 \; 0 \; 0 \; 0]$$

Finally, equations (14a) and (14b) are combined by defining the augmented state $x(t_k):=[x_{phy}(t_k)|e(t_k)]^T$ and the augmented error $v(t_k):=[v_{phy}(t_k)|B \cdot \in (t_k)]^T$.

The augmented model update equation reads $$x(t_{k+i})=f(x(t_{k+1}),u(t_{k+1}),t,\theta)+v(t_k) \tag{15}$$

V. Realtime Glucose Prediction Through Particle Filter

Up to this point, we focused on estimating the parameters of the physiological model of a T1D subject, to capture the patient-specific dynamics. This process can be done "offline" using the available information obtained from retrospective patient data.

In this section, we will present how we used such a personalized model to predict, in real-time, future glucose concentrations. This task has to be performed "online", so we resorted to a sequential algorithm that at each timestep $t_k$, when a new measurement $y(t_k)=CGM(t_k)$ becomes available, updates the current estimate of the model state $x(t_k)$ and uses it to infer future glucose concentration. In particular, we employ the particle filter (PF), which is a sequential Bayesian prediction technique capable of handling the nonlinear structure of the model.

PF is based on the recursive update of the posterior probability function $p(x(t_k)|y(t_{1:k}),u(t_{1:k}))$ where y $(t_{1:k})$ is a shorthand for the variables $y(t_1), \ldots, y(t_k)$ and $u(t_{1:k})$ indicates $u(t_1), \ldots, u(t_k)$.

The recursive update of p $(x(t_{k-1})|y(t_{1:k-1}), u(t_{1:k-1}))$ is performed through two fundamental steps, i.e., one step-ahead prediction and measurement update.

The one step-ahead prediction step assumes that the posterior probability $p(x(t_{k-1})|y(t_{1:k-1}), u(t_{1:k-1}))$ is available at time $t_{k-1}$ and uses such a posterior probability to infer $$p(x(t_k)|y(t_{1:k-1}),u(t_{1:k}))$$

Then, when at time $t_k$ a new measurement, $y(t_k)$, becomes available, in the measurement update step such a measurement is used to compute the posterior probability $$p(x(t_k)|y(t_{1:k}),u(t_{1:k})).$$

The two steps are then repeated for each available measurement in the dataset. PF performs these steps using a sampled approximation of the probability functions at play:

$$p(x(t_{k-1}) \mid y(t_{1:k-1}),$$

$$u(t_{1:k-1})) \approx \sum_{p=1}^{P} w^P(t_{k-1}) \delta(x(t_{k-1}) - x^P(t_{k-1})).$$

where $\{x^P(t_{k-1})\}_{p=1}^{P}$ is a set of P points, called "particles", in the support of $p(x(t_{k-1})|y(t_{1:k-1}), u(t_{1:k-1}))$. Each particle is associated to a weight $\{w^P(t_{k-1})\}_{p=1}^{P} \Sigma_p w^P(t_{k-1}) = 1$, and $$p(x(t_k) \mid y(t_{1:k-1}),$$

$$u(t_{1:k})) \approx \sum_{p=1}^{P} w^{*P}(t_k) \delta(x(t_k) - x^P(t_k)).$$

where $\{x^P(t_k)\}_{p=1}^{P}$ are the P particles representing $p(x(t_k)|y(t_{1:k-1}), u(t_{1:k}))$, each associated to a weight $\{w^{*P}(t_k)\}_{p=1}^{P}$, $\Sigma_p w^{*P}(t_k) = 1$.

When dealing with state space models such as (15), the one step-ahead prediction step of the PF is particularly convenient. It can be shown that $$p(x(t_k)|y(t_{1:k-1}),u(t_{1:k})) = \int p(x(t_k)|x(t_{k-1}))$$
$$p(x(t_{k-1})|y(t_{1:k-1}),u(t_{1:k-1}))dx(t_{k-1})$$

where $p(x(t_k)|x(t_{k-1}))$ is fully described by the state update equations of (15). Regarding the measurement update step, it is possible to demonstrate that it holds $$p(x(t_k)|y(t_{1:k}),u(t_{1:k})) \propto p(y(t_k)|x(t_k),u(t_{1:k}))_p$$
$$(x(t_k)|y(t_{1:k-1}),u(t_{1:k}))$$

where $p(y(t_k)|x(t_k),u(t_{1:k}))$ is the likelihood function that is fully specified by (14c).

Details on how these quantities are calculated in practice are reported in the "Implementation Details" section.

As an additional result, the posterior probability $p(x(t_k)|y(t_{1:k}),u(t_{1:k}))$ is furtherly used by the PF to compute the posterior probabilities $$p(x(t_{k+i})|y(t_{1:k}),u(t_{1:k+i})), \forall i = 1, \dots, PH$$

describing the state distribution predicted i steps-ahead in time up to PH steps ahead (with PH the prediction horizon).

In particular, it is possible show that for state space models like (15)

$$p(y(t_{k+i})|y(t_{1:k}),u(t_{1:k+i})) = p(y(t_{k+i})|x(t_{k+i}),$$
$$\forall i = 1, \dots, PH$$

that is completely specified by equation (14c).

Finally, a point estimate of future CGM values at time $t_{k+i}$, $i = 1, \dots, PH$ can be derived using the expectation of the posterior:

$$\hat{y}(t_{k+i}|t_k) = E[p(y(t_{k+i})|x(t_{k+i}))], \forall i = 1, \dots, PH.$$

A. Implementation Details

In the following, we present the numerical scheme implemented by PF to perform the one step-ahead prediction, measurement update, and multiple step-ahead prediction.

One step-ahead prediction step. Recalling that, at time $t_{k-1}$, $p(x(t_{k-1})|y(t_{1:k-1}),u(t_{1:k-1}))$ is available in a sampled form defined by set of P particles $\{x^P(t_{k-1})\}_{p=1}^{P}$ with associated weights $\{w(t_{k-1})^P\}_{p=1}^{P}$, $\Sigma_p w(t_{k-1})^P = 1$ such that $$p(x(t_{k-1}) \mid y(t_{1:k-1}),$$

$$u(t_{1:k-1})) \approx \sum_{p=1}^{P} w^P(t_{k-1}) \delta(x(t_{k-1}) - x^P(t_{k-1})),$$

PF performs the one step-ahead prediction step by drawing a new set of particles $\{x^P(t_k)\}_{p=1}^{P}$ from $p(x(t_k)|x(t_{k-1}))$:

$$x^P(t_k) \sim p(x^P(t_k)|x^P(t_{k-1})) \tag{16}$$

This probability is specified by (15):

$$p(x^P(t_k)|x^P(t_{k-1})) \sim N(f(x^P(t_{k-1}),u,t_{k-1},\theta),\Sigma_v).$$

In view of this, to draw the new set of particles it is sufficient to let each particle $x^P(t_{k-1})$ evolve according to model (15), and corrupt it with a realization of the noise v.

Measurement update step. The PF algorithm sets the weight $w^{*P}(t_k)$ of each p-th particle $x^P(t_k)$ to the likelihood function evaluated on $x^P(t_k)$ $$w^{*P}(t_k) = p(y(t_k)|x^P(t_k),u(t_{1:k})). \tag{17}$$

In particular, from equation (14c) and the statistics of the stochastic modelling error e, $p(y(t_k)|x^P(t_k),u(t_{1:k}))$ is defined as:

$$p(y(t_k)|x(t_k),u(t_{1:k})) = N(y(t_k) - y^P(t_k),SD_e). \tag{18}$$

where $y^P(t_k)$ is obtained using (14c).

Weights are then normalized such that $\Sigma_p w^{*P}(t_k) = 1$.

This provides a sampled form representation of the posterior density $$p(x(t_k) \mid y(t_{1:k-1}),$$

$$u(t_{1:k})) \approx \sum_{p=1}^{P} w^{*P}(t_k) \delta(x(t_k) - x^P(t_k)).$$

Re sampling step. To improve the accuracy of PF, the measurement update step is completed by updating the set of particles. Specifically, $\{x^P(t_k)\}_{p=1}^{P}$ are substituted with a new set of P particles, $\{x^{*P}(t_k)\}_{p=1}^{P}$ generated from the sampled representation of $p(x(t_k)|y(t_{1:k-1}),u(t_{1:k}))$ such that $Pr(x^{*P}(t_k) = x^P(t_k)) = w^{*P}(t_k)$. This step is performed by a well-established resampling algorithm described in G. Kitagawa, "Monte carlo filter and smoother for non-gaussian non-linear state space models," J. Comput. Graph. Statist., vol. 5, no. 1, pp. 1-25, 1996.

As a result, all new particles $\{x^P(t_k)\}_{p=1}^{P}$ are associated to the same weight $w^{*P}(t_k) = 1/P$, thus the approximation of $p(x(t_k)|y(t_{1:k-1}),u(t_{1:k}))$ simplifies to $$p(x(t_k) \mid y(t_{1:k-1}),$$

$$u(t_{1:k})) \approx \frac{1}{P} \sum_{p=1}^{P} \delta(x(t_k) - x^P(t_k)).$$

Multiple steps-ahead prediction. Multiple steps ahead predictions can be obtained as follows. First, the probabilities $p(x(t_{k+1})|y(t_{1:k}),u(t_{1:k+i})), \forall, i = 1, \dots, PH$ are obtained in sampled form starting from $p(x(t_k)|y(t_{1:k}),u(t_{1:k}))$ and propagating the P particles $\{x^P(t_k)\}_{p=1}^{P}$ i steps ahead as we did in the one step-ahead prediction step.

Then, using equation (14c), the set of particles $\{y^P(t_{k+i}|t_k)\}_{p=1}^{P}$ is computed and used to obtain $p(y(t_{k+1})|y(t_{1:k}), u(t_{1:k+i}))\forall, i = 1, \dots, PH$ in sampled form.

Finally, a point estimate of glucose i steps-ahead, $y(t_{k+i})$, is obtained as the average computed over the sampled form of $p(y(t_{k+i})|y(t_{1:k}), u(t_{1:k+i})$, i.e.:

$$\hat{y}(t_{k+i}|t_k) = \frac{1}{P}\sum_{p=1}^{P} y^p(t_{k+i}|t_k), \forall\, i = 1, \ldots, PH.$$

The implemented PF is summarized in Algorithm (2).

---

Algorithm 2: Particle Filter

```
k ← 1;
x_{t0} = N(x_{ss}, Σ_v));
repeat
    Step 1: One step-ahead prediction;
    for p ← 1 to P do
        sample x^p(t_k) from
            N(f(x^p(t_{k-1}), u, t_{k-1}, θ), Σ_v));
    end
    Step 2: Measurement update;
    for p ← 1 to P do
        compute w*^p (t_k) = N(y(t_k) − y^p(t_k), SD_a);
    end
    normalize w*^p(t_k) = w*^p(t_k)/Σ_p w*^p(t_k);
    Step 3: Resampling;
    sample {x*^p(t_k)}_{p=1}^P s.t. Pr(x*^p(t_k) = x^p(t_k)) =
        w*^p (t_k);
    set {x^p(t_k)}_{p=1}^P = {x^p*(t_k)}_{p=1}^P;
    Step 4: Multiple steps-ahead prediction;
    for p ← 1 to P do
        compute y^p(t_{k+i}|t_k), ∀i = 1, . . ., PH;
    end
    compute ŷ(t_{k+i}|t_k) = 1/P Σ_{p=1}^P y^p(t_{k+1}|t_k), ∀i =
        1, . . ., PH;
    k ← k + 1
until k ≤ D;
```

---

VI. Methodology Assessment

A. The Simulated Dataset

T1DS is a software tool that has been accepted by the FDA as a substitute to pre-clinical trials for closed-loop insulin delivery strategies and open-loop therapy. It provides a population of 100 virtual adult subjects, each characterized by a different vector of physiological parameters to capture the inter-/intra-subject variability of T1D population. In this particular example described herein, we used the most updated version of the simulator, capable to better account for inter-/intra-patient variability (i.e., changes over time in a patient's physiology, and patient behaviour. Using the T1DS, two weeks of synthetic data have been generated for 100 virtual adults, simulating the so-called Sensor Augmented Pump therapy (SAP). In this therapy regimen insulin is administered to the patient by an insulin pump as the sum of two components: the first component is the basal insulin infusion rate, a fixed daily pattern adjusted to each patient by the clinician; the second component consists of multiple insulin doses administered at each meal to counterbalance the corresponding glucose increase. The amount of insulin injected is proportional to the estimated carbohydrate intake (CHO) and pre-prandial glucose measurement.

In our simulated scenario, each subject ate 3 meals per day taking place with uniform probability in the intervals [06:30, 08:30] (breakfast), [12:00, 14:00] (lunch), and [19:30, 21:30] (dinner) with CHO consumption uniformly distributed in [20, 60], [50, 90], and [50, 90] g, respectively. A simple safety protocol, consisting in consuming 15 g of fast-acting CHO each 15 minutes while the patient's measured glucose is below 70 mg/dl, was implemented to treat hypoglycemia. Finally, the measurement error of the CGM sensor was modeled as proposed in A. Facchinetti, S. Del Favero, G. Sparacino, and C. Cobelli, "Model of glucose sensor error components: Identification and assessment for new dexcom g4 generation devices," Med. Biol. Eng. Comput., vol. 53, no. 12, pp. 1259-1269, 2015. The obtained in silico dataset has been split into training and test set by assigning the first week of data to the former and the second week of data to the latter.

B. Prediction Approaches Used for Comparison

As a baseline for prediction accuracy, we considered with two state-of-the-art black-box models: we trained on the same training data an Auto Regressive with eXogenous input (ARX) model of order 5, and an Auto Regressive Integrated Moving Average with eXogenous input (ARIMAX) model of order (5,5,1) both having two inputs, insulin infusion I(t) and carbohydrate intake CHO(t), and one output, the glucose concentration CGM.

C. Assessment Metrics

Evaluation of prediction accuracy has been performed in the test set by comparing the obtained glucose predictions with the actual CGM values using different PH. In this work, three metrics have been considered: the root mean square error (RMSE), the coefficient of determination (COD), and the time gain (TG). These metrics, frequently used in the literature, are defined as follows:

$$RMSE(i) = \frac{1}{\sqrt{m}}\|y(t_{k+i}) - \hat{y}(t_{k+i}\,|\,t_k)\|_2, \forall\, i = 1, \ldots, PH.$$

where $\|\cdot\|_2$ denotes the $\ell_2$ norm. The larger the RMSE the worst the prediction.

$$COD(i) = 100\cdot\left(1 - \frac{\|y(t_{k+i}) - \hat{y}(t_{k+i}\,|\,t_k)\|_2^2}{\|y(t_{k+i}) - \bar{y}(t_{k+i})\|_2^2}\right),$$
$$\forall\, i = 1, \ldots\, PH.$$

where $\bar{y}(t_{k+i})$ is the sample mean of the glucose measurement timeseries. COD depends on the RMSE, normalized for the signal sample variance. COD is at most COD=100%, in case of perfect prediction (RMSE=0 mg/dl) and decreases when RMSE increases.

$$TG(i) = i\cdot T_s - \text{delay}(y(t_{k+i}), \hat{y}(t_{k+i})), \forall i = 1, \ldots, PH.$$

where delay($s_1(t_k)$, $s_2(t_k)$) [min] quantifies the delay between two signals $s_1(t_k)$ and $s_2(t_k)$ and is based on the cross-correlation (xcorr), a measure of similarity of the two signals. Specifically, the delay is defined as the temporal shift $\tau$ that maximizes the cross-correlation (xcorr) between $s_1$ and a $\tau$-shifted version of $s_2$:

$$\text{delay}(s_1(t_k), s_2(t_k)) = \text{argmax}_\tau[\text{xcorr}(s_1(t_k), s_2(t_k-\tau)]$$

The higher TG, the more prompt and useful the prediction and TG=0 means that the model prediction is comparable to looking at the current glucose level.

Performance metrics of PF are compared against ARX and ARIMAX using a paired t-test unless the hypothesis of normal distribution was rejected by a Lilliefors test (p-value >0.05). In this case, Wilcoxon ranksign test was used. Reported p-values are two-tailed and considered statistically significant when <0.05.

TABLE II

Comparison between the performance metrics (median [iqr]) obtained using ARX, ARIMAX, and PF on the in silico population for PH = 30, 60, 90, 120 min. Best average results are in bold weight.

| Metric | Methodology | PH [min] | | | |
|--------|-------------|----------|----------|----------|----------|
| | | 30 | 60 | 90 | 120 |
| RMSE | PF | 13.85 | 21.27 | 26.14 | 29.83 |
| | | [11.93, 15.89] | [17.95, 24.81] | [63.82, 78.08] | [26.06, 36.52] |
| | ARX | 14.73 | 25.12 | 33.97 | 41.61 |
| | | [13.42, 16.94] | [21.55, 29.67] | [28.09, 40.28] | [33.89, 48.26] |
| | | p < 0.0001 | p < 0.0001 | p < 0.0001 | p < 0.0001 |
| | ARIMAX | 13.26 | 21.81 | 28.92 | 35.64 |
| | | [12.07, 15.25] | [18.50, 25.96] | [24.24, 35.11] | [29.67, 44.12] |
| | | p = 0.22 | p = 0.03 | p < 0.0001 | p < 0.0001 |
| COD | PF | 91.54 | 81.36 | 70.80 | 61.06 |
| | | [89.18, 93.89] | [75.65, 85.66] | [63.82, 78.08] | [51.83, 71.82] |
| | ARX | 89.35 | 71.50 | 50.50 | 28.07 |
| | | [87.53, 92.18] | [66.10, 77.86] | [40.20, 59.85] | [14.21, 40.13] |
| | | p < 0.0001 | p < 0.0001 | p < 0.0001 | p < 0.0001 |
| | ARIMAX | 91.61 | 78.19 | 60.18 | 40.36 |
| | | [88.54, 94.20] | [70.46, 84.80] | [49.79, 72.27] | [22.77, 60.08] |
| | | p = 0.28 | p = 0.03 | p < 0.0001 | p < 0.0001 |
| TG | PF | 30.0 | 60.0 | 90.0 | 120.0 |
| | | [25.0, 30.0] | [55.0, 60.0] | [80.0, 90.0] | [105.0, 120.0] |
| | ARX | 15.0 | 20.0 | 22.5 | 25.0 |
| | | [10.0, 20.0] | [25.0, 40.0] | [35.0, 70.0] | [55.0, 110.0] |
| | | p < 0.0001 | p < 0.0001 | p < 0.0001 | p < 0.0001 |
| | ARIMAX | 25.0 | 50.0 | 80.0 | 110.0 |
| | | [15.0, 30.0] | [30.0, 55.0] | [37.5, 85.0] | [35.0, 120.0] |
| | | p < 0.0001 | p < 0.0001 | p < 0.0001 | P < 0.0001 |

D. Results

Figure 6A:
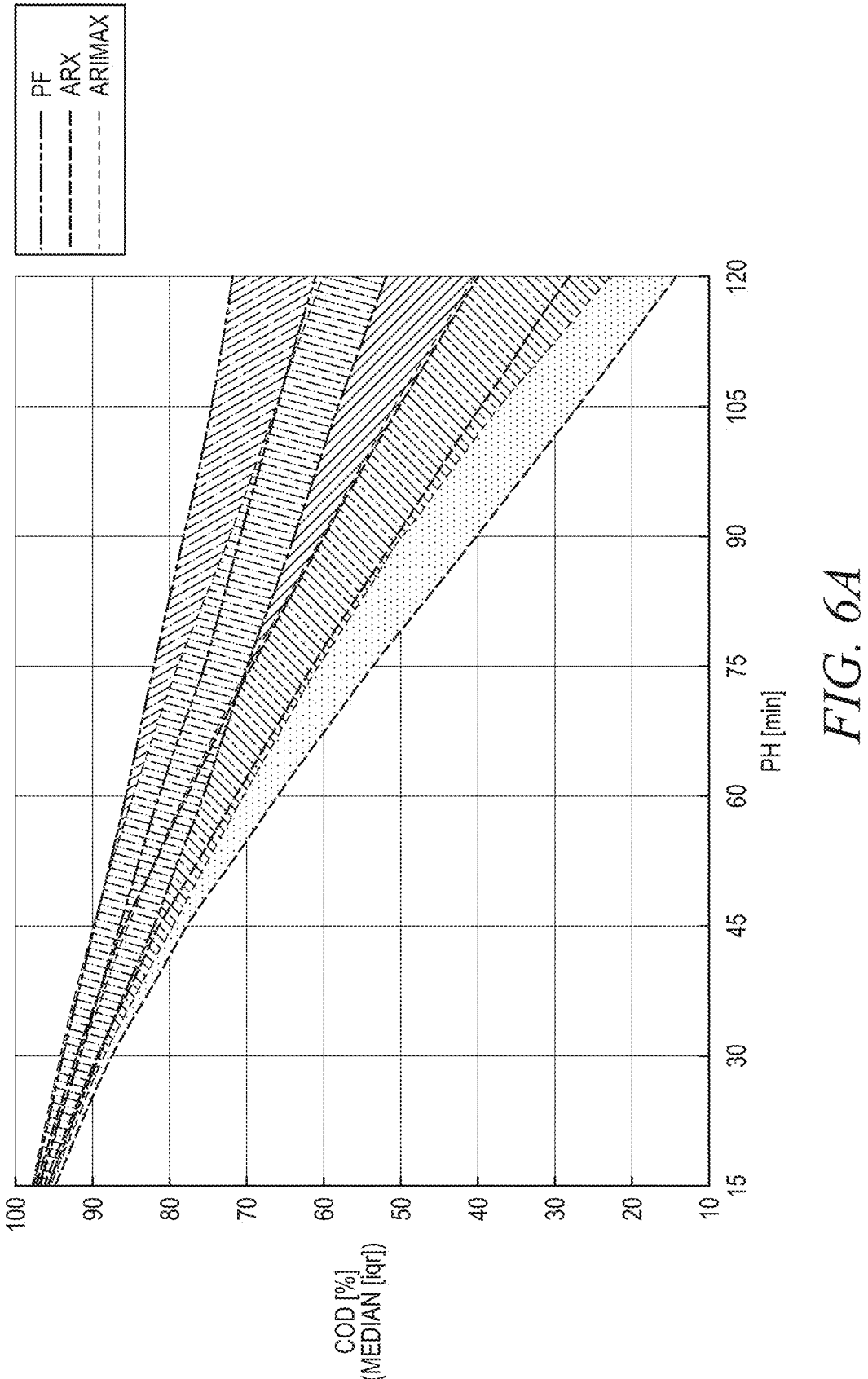
FIG. 6A shows the coefficient of determination (COD) obtained with ARX, ARIMAX, and PF for different PH, from 15 min up to 120 min.
Figure 6B:
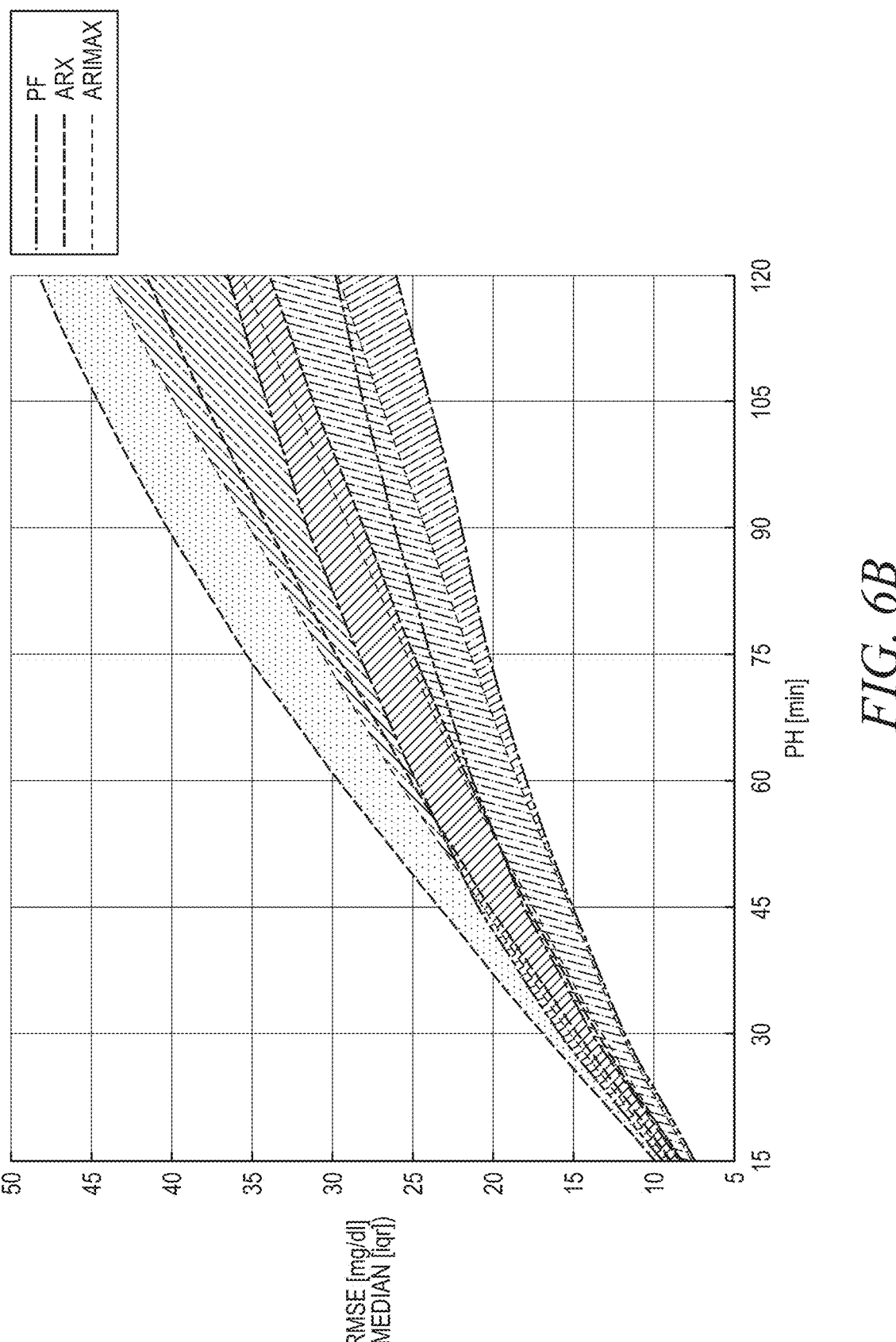
FIG. 6B shows the root mean square error (RMSE) obtained with ARX, ARIMAX, and PF for different PH, from 15 min up to 120 min.

FIGS. 6A and 6B show RMSE and COD obtained with ARX, ARIMAX, and PF for different PH, from 15 min up to 120 min. The tick line represents the median over the population, while the area between the 25th and 75th percentile is shaded. The same information is reported in Table II for PH=30, 60, 90 and 120 min, that includes also the p-values.

Compared to ARX, PF achieves significantly better outcomes (p<0.05) for all considered metrics and PH, the higher PH the bigger the improvement. In detail, the average $\Delta RMSE=RMSE_{PF}-RMSE_{ARX}$ is −1.47 mg/dl (−6%), −3.85 mg/dl (−15%), −7.83 mg/dl (−23%), and −11.78 mg/dl (−28%) for PH=30, 60, 90, and 120 min, respectively. The same considerations hold when the prediction accuracy is evaluated in terms of average $\Delta COD$ which improved by 2.19% (2%), 9.86% (14%), 20.30% (40%), and 32.99% (118%) for PH=30, 60, 90, and 120 min, respectively. Focusing on $\Delta TG$, PF remarkably improves the outcomes by 15.0 min (100%), 40.0 min (200%), 67.5 min (300%), 95.0 min (380%) for PH=30, 60, 90, and 120 min, respectively.

Comparing PF with ARIMAX, the former achieves significantly better RMSE and COD for PH>30 min, the higher PH the bigger the improvement. In detail, PF improved significantly (p<0.05) $\Delta RMSE=RMSE_{PF}-RMSE_{ARIMAx}$ by −0.54 mg/dl (−2%), −2.78 mg/dl (−10%), and −5.81 mg/dl (−16%) for PH=60, 90, and 120 min respectively, and improved significantly (p<0.05) $\Delta COD$ by 3.17% (4%), 10.62% (18%), and 20.70% (51%) for PH=60, 90, and 120 min, respectively. At PH=30 min, the performances are not statically significantly different: p-value(RMSE, PH=30 min)=0.22, p-value(COD, PH=30 min)=0.28.

Finally, PF improved significantly (p<0.05) $\Delta TG$ by 5.0 min (20%), 10.0 min (20%), 10.0 min (13%), and 10.0 min (9%) for PH=30, 60, 90, and 120 min, respectively. Notably, the PF allows, on average, to achieve TG equal to PH.

VII. Alternative Embodiments

The individualized model-based prediction scheme presented herein in connection with the flowchart of FIG. 1 has been illustrated using exemplary examples of a particular individualized nonlinear physiological model (a maximal model such as the UVa/Padova T1D Simulator), a particular parameter estimation technique (MCMC) and a particular nonlinear prediction scheme (a particle filter methodology). More generally, the individualized model-based prediction scheme may employ a variety of alternative parameter estimation techniques and a variety of alternative nonlinear prediction schemes may be used in combination with different individualized nonlinear physiological models. For example, in some embodiments the parameter estimation technique that is employed may be a maximum likelihood technique or a prediction error minimization method. Likewise, in some embodiments the nonlinear prediction scheme that is employed may be an extended Kalman filter technique or an unscented Kalman filter technique.

VIII. Conclusion

Personalized real-time prediction of glucose concentration in T1D is important to enable effective proactive therapeutics. We have presented a methodology that uses a personalized physiological model to achieve this goal. In some embodiments this gray-box nonlinear model is handled in a Bayesian framework comprising two main phases. In the first phase, we use MCMC, for example, to identify patient-specific parameters of a physiological model of a T1D subject. Then, in the second phase, the personalized model is used by a particle filter or other nonlinear prediction scheme to infer future glucose data. The first phase may conducted offline, retrospectively processing patients historical data. The second phase may run online as new patient data becomes available.

The various operations of methods described above may be performed by any suitable means capable of performing the operations, such as various hardware and/or software component(s), circuits, and/or module(s). Generally, any operations illustrated in the figures may be performed by corresponding functional means capable of performing the operations.

The various illustrative logical blocks, modules and circuits described in connection with the present disclosure may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general-purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on non-transitory computer-readable medium. By way of example, and not a limitation, such non-transitory computer-readable media can comprise RAM, ROM, EEPROM, CD-ROM or other optical disk storage, magnetic disk storage or other magnetic storage devices.

The methods disclosed herein comprise one or more steps or actions for achieving the described methods. The method steps and/or actions may be interchanged with one another without departing from the scope of the claims. In other words, unless a specific order of steps or actions is specified, the order and/or use of specific steps and/or actions may be modified without departing from the scope of the claims.

Certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All references cited herein are incorporated herein by reference in their entirety. To the extent publications and patents or patent applications incorporated by reference contradict the disclosure contained in the specification, the specification is intended to supersede and/or take precedence over any such contradictory material.

Headings are included herein for reference and to aid in locating various sections. These headings are not intended to limit the scope of the concepts described with respect thereto. Such concepts may have applicability throughout the entire specification.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

The invention claimed is:

1. A method of predicting future blood glucose concentrations of an individual patient having a continuous glucose monitoring (CGM) sensor, comprising:

selecting, by a processor, an individualized nonlinear physiological model of glucose-insulin dynamics, the selected individualized nonlinear physiological model having a plurality of model parameters whose values are to be determined;

estimating, by the processor, population-based values of a first subset of the plurality of model parameters from a priori population data, wherein the estimated population-based values of the first subset relate to at least one of insulin absorption or glucose absorption;

estimating, by the processor, personalized values of a second subset of the model parameters by applying a parameter estimation technique to a priori information about a probability distribution of each parameter of the second subset and data for the individual patient, the data for the individual patient comprising insulin infusion information for the individual patient and carbohydrate intake information for the individual patient;

obtaining, by the processor, an a posteriori probability function based on past glucose measurements of the individual patient from the CGM sensor, the estimated population-based values of the first subset of the plurality of model parameters, and the estimated personalized values of the second subset of the plurality of model parameters;

receiving, by the processor, a current glucose measurement of the individual patient from the CGM sensor;

updating, by the processor, the posteriori probability function based on the current glucose measurement;

applying, by the processor, a particle filter to the selected individualized nonlinear physiological model using the updated a posteriori probability function to obtain a predicted blood glucose concentration of the individual patient at a future time;

generating, by the processor, a notification based on the predicted blood glucose concentration indicating upcoming dysglycemia, the notification comprising a proactive alert of the upcoming dysglycemia; and causing, by the processor, the notification to be output on a device associated with the individual patient.

2. The method of claim 1, wherein the parameter estimation technique is a Markov Chain Monte Carlo (MCMC) Bayesian estimator.

3. The method of claim 1, wherein the parameter estimation technique is selected from the group consisting of a maximum a posteriori technique, a maximum likelihood technique and a prediction error minimization technique.

4. The method of claim 1, wherein the selected individualized nonlinear physiological model includes a subcutaneous insulin absorption sub-model, an oral glucose absorption sub-model and a glucose-insulin kinetics model.

5. The method of claim 4, wherein the subcutaneous insulin absorption sub-model includes a first model parameter specifying a value of insulin distribution and a second model parameter specifying a delay in an appearance of insulin in a first compartment, the first and second model parameters being in the first subset of the plurality of model parameters having the estimated population-based values.

6. The method of claim 5, wherein the subcutaneous insulin absorption sub-model includes a third model parameter specifying a diffusion rate constant from a first to a second compartment and a fourth model parameter specifying a rate constant of subcutaneous insulin absorption from the second compartment to plasma, the third and fourth model parameters being in the second subset of the plurality of model parameters having the estimated personalized values.

7. The method of claim 1, wherein the selected individualized nonlinear physiological model is a maximal physiological model in which selected ones of the plurality of model parameters are neglected.

8. The method of claim 1, further comprising augmenting the selected individualized nonlinear physiological model with a residual error model to describe residual modeling errors.

9. The method of claim 8, wherein the residual modeling errors are modeled as an Auto regressive Integrated Moving Average (ARIMA) of order (5,5,1).

10. The method of claim 8, wherein the residual error model has model parameters estimated using a predicted error method (PEM).

11. The method of claim 1, wherein the predicted blood glucose concentration is predicted at a plurality of different times.

12. A computer-program product comprising a non-transitory computer-usable medium having computer-readable program code embodied therein, the computer-readable program code adapted to be executed to implement a method of predicting future blood glucose concentrations of an individual patient having a continuous glucose monitoring (CGM) sensor, the method comprising:

selecting an individualized nonlinear physiological model of glucose-insulin dynamics, the selected individualized nonlinear physiological model having a plurality of model parameters whose values are to be determined;

estimating population-based values of a first subset of the plurality of model parameters from a priori population data, wherein the estimated population-based values of the first subset relate to at least one of insulin absorption or glucose absorption;

estimating personalized values of a second subset of the model parameters by applying a parameter estimation technique to a priori information about a probability distribution of each parameter of the second subset and data for the individual patient, the data for the individual patient comprising insulin infusion information for the individual patient and carbohydrate intake information for the individual patient;

obtaining an a posteriori probability function based on past glucose measurements of the individual patient from the CGM sensor, the estimated population-based values of the first subset of the plurality of model parameters, and the estimated personalized values of the second subset of the plurality of model parameters;

receiving a current glucose measurement of the individual patient from the CGM sensor;

updating the posteriori probability function based on the current glucose measurement;

applying a particle filter to the selected individualized nonlinear physiological model using the updated a posteriori probability function to obtain a predicted blood glucose concentration of the individual patient at a future time;

generating a notification based on the predicted blood glucose concentration indicating upcoming dysglycemia, the notification comprising a proactive alert of the upcoming dysglycemia; and causing the notification to be output on a device associated with the individual patient.

13. The computer-program product of claim 12, wherein the parameter estimation technique is a Markov Chain Monte Carlo (MCMC) Bayesian estimator.

14. The computer-program product of claim 12, wherein the parameter estimation technique is selected from the group consisting of a maximum a posteriori technique, a maximum likelihood technique and a prediction error minimization technique.

15. The computer-program product of claim 12, wherein the selected individualized nonlinear physiological model includes a subcutaneous insulin absorption sub-model, an oral glucose absorption sub-model and a glucose-insulin kinetics model.

16. The computer-program product of claim 15, wherein the subcutaneous insulin absorption sub-model includes a first model parameter specifying a value of insulin distribution and a second model parameter specifying a delay in an appearance of insulin in a first compartment, the first and second model parameters being in the first subset of the plurality of model parameters having the estimated population-based values.

17. The computer-program product of claim 16, wherein the subcutaneous insulin absorption sub-model includes a third model parameter specifying a diffusion rate constant from a first to a second compartment and a fourth model parameter specifying a rate constant of subcutaneous insulin absorption from the second compartment to plasma, the third and fourth model parameters being in the second subset of the plurality of model parameters having the estimated personalized values.

18. The method of claim 1, wherein the notification comprises a recommended treatment to mitigate the upcoming dysglycemia indicated by the predicted blood glucose concentration.

19. The method of claim 1, wherein the device associated with the individual patient comprises the processor.

20. The method of claim 1, wherein the causing comprises communicating, by the processor, the notification to the device associated with the individual patient.

* * * * *